United States Patent
Li et al.

(10) Patent No.: US 9,226,911 B2
(45) Date of Patent: *Jan. 5, 2016

(54) METHOD OF REDUCING WEIGHT USING COMPOSITION CONTAINING FUCOXANTHIN EXTRACT

(71) Applicant: BEIJING GINGKO GROUP BIOLOGICAL TECHNOLOGY CO., LTD., Beijing (CN)

(72) Inventors: Yanmei Li, Beijing (CN); Qinghua Liu, Beijing (CN)

(73) Assignee: BEIJING GINGKO GROUP BIOLOGICAL TECHNOLOGY CO., LTD., Beijing (CN)

(*) Notice: Subject to any disclaimer, the term of this patent is extended or adjusted under 35 U.S.C. 154(b) by 397 days.

This patent is subject to a terminal disclaimer.

(21) Appl. No.: 13/845,176

(22) Filed: Mar. 18, 2013

(65) Prior Publication Data

US 2013/0224240 A1    Aug. 29, 2013

Related U.S. Application Data

(62) Division of application No. 13/144,765, filed as application No. PCT/CN2009/000073 on Jan. 19, 2009, now Pat. No. 8,454,970.

(51) Int. Cl.
A61K 36/00 (2006.01)
A61K 31/336 (2006.01)
A61K 31/355 (2006.01)
A61K 31/737 (2006.01)
A61K 36/02 (2006.01)

(52) U.S. Cl.
CPC ............ *A61K 31/336* (2013.01); *A61K 31/355* (2013.01); *A61K 31/737* (2013.01); *A61K 36/02* (2013.01)

(58) Field of Classification Search
None
See application file for complete search history.

(56) References Cited

U.S. PATENT DOCUMENTS

2004/0102385 A1* 5/2004 Ames et al. ............... 514/25
2005/0129708 A1* 6/2005 Fujii et al. ................ 424/195.15
2008/0206275 A1* 8/2008 Ramazanov et al. .... 424/195.17

* cited by examiner

*Primary Examiner* — Qiuwen Mi
(74) *Attorney, Agent, or Firm* — The PL Law Group, PLLC

(57) ABSTRACT

A method of reducing a weight of a subject includes administering to the subject in need thereof a composition comprised of fucoxanthin extract and at least one selected from the group consisting of tocotrienol, fucoidan and a combination thereof, wherein the subject is a mammal.

20 Claims, No Drawings

METHOD OF REDUCING WEIGHT USING COMPOSITION CONTAINING FUCOXANTHIN EXTRACT

CROSS REFERENCE TO RELATED APPLICATION

This application is a divisional application of application Ser. No. 13/144,765, which is the National Stage of International Application No. PCT/CN2009/000073 with an International Filing Date of Jan. 19, 2009, and which claims all benefits accruing under 35 U.S.C. §365(c) from the PCT International Application PCT/CN2009/000073 with an International Filing Date of Jan. 19, 2009, the entire contents of which are incorporated herein by reference.

TECHNICAL FIELD

This invention involves compositions containing algae extract, especially a composition containing fucoxanthin extract having a weight reducing function.

BACKGROUND

Natural carotenoids such as β-carotene, lycopene, lutein and fucoxanthin were extensively studied because of their anti-tumor characteristics as well as prominent free radical elimination functions. Recent studies found that some carotenoids had more specific and unique pharmacological functions. For instance, some reports alleged that fucoxanthin had a weight reducing function. Fucoxanthin, also called pheophytin, is the pigment contained in brown diatoms, chrysophrys and yellow-green algae. It takes part in the photosynthesis as parts of the photochemical system II. Separated from the algae, it is red-brown crystal. Being a kind of xanthophylls, it renders brown color to the brown algae and thus is the characteristic pigment in brown algae. It is also sporadically contained in the diatoms and other algae. Sometimes it is confounded with phycophaein, however the latter is considered to be the characteristic water-soluble pigment in the brown algae, it seems to be a imaginary material, and is an yellow-brown oxidation product of a phenolic compound contained in the brown algae after death of these plants. Therefore fucoxanthin and phycophaein are essentially different substances. The results of studies showed that fucoxanthin regulates high expression of the uncoupling protein (UCP1) gene in the animal white adipose tissue (WAT), causing the decrease of fat contents in the entrails. Experiments verified that fucoxanthin reduced the amount of WAT in rats and fat KK-Ay mouse. Mediated by fucoxanthin, the expression of UCP1 in the WAT expedites the oxidation of fatty acids. (Maeda H, Hosokawa M, Biochem. Biophys. Res. Commun., 2005, 332(2):392-397; Maeda H, Hosokawa M, Int. J. Mol. Med., 2006, 18(1):147-152; Miyashita K, J. marine Bioscience and Biotechnology, 2006, 1(1):48-58). In spite of all the recognition to the weight reducing function of fucoxanthin, however, it should be recognized that weight-reducing is a compositive process with many physiologic biochemical reactions involved in vivo and the application of a single component cannot result in an ideal effect. Therefore, a fucoxanthin composition with distinctively synergic function is needed in this field to exert a weight reducing function.

Tocotrienols are a kind of functional components contained in palm oil and rice bran oil, their chemical structure is similar to tocopherol. Recent studies showed that they are superior in physiologic functions to tocopherol. Vitamin E is very important in every growth phases of various animals, and is absolutely necessary for the exertion of optimal function of the procreation, muscle, nervous and immune systems. Among vitamins, α-tocopherol, usually called Vitamin E, has the highest activity and widest distribution and is the most representative, hence it has been the focal research subject. However, recent studies found that tocotrienols showed more prominent characteristics than α-tocopherol in some cases, such as anti-oxidation, anti-tumor and cholesterol-lowering activities. These special functions of tocotrienols are related to its structure. As tocotrienols have an unsaturated side chain, they are able to more effectively penetrate into the organs containing saturated fatty acid layers, such as the brain and liver, and it is easier for them to distribute into the lipid layers of the cell membranes, thereby performing a better functions of anti-oxidation as well as cleaning up free radicals. To date tocotrienols are studied in depth abroad, whereas they are studied relatively less in China, especially on their efficacy in the applications in weight reduction.

The seas are vast in our Earth and the sources of alga plants in the sea are abundant, fucoidans are gradually becoming one of the main sources of biological polysaccharides. Owing to the special living environment of the sea algae, fucoidans have some unique biological activities, for example, laminarin is capable of decreasing the superoxide content in the spleen and increasing the activities of superoxide dismutase (SOD) as well as catalase (CAT), thereby achieving antitumor purpose; porphyra polysaccharide and propylene glycol mannate sulfate (PGMS) have the functions of anti-thrombus and improving microcirculation; laminarin and porphyra polysaccharide etc. may have the function of protecting the cells of organisms. More and more researches have shown that fucoidans have enormous prospect of being exploited and applied. Brown algae polysaccharides, included brown algae carbohydrate gum, brown algae gum and brown algae starch, are the important components of fucoidans.

In recent 10 years, Japanese scientists studied brown algae extensively and thoroughly with thousands of paper published. These papers involve the analysis of chemical constituents of brown algae, the researches on their pharmacological effects and their potential medicinal applications as well as new applications in health protection, etc. Researchers found that brown algae polysaccharides have many physiological activities including effects of antitumor/increase of human immunity, anti-allergy, liver-protection, anti-coagulation, cleaning-up of the physiological environment of intestinal tracts, decreasing the blood fat content, anti-ulcer, decreasing blood sugar, skin wetness reservation, etc. Therefore, it was proposed that fucoidan and the like have the potential to be the materials of many new medicines.

Among various brown algae polysaccharide materials separated to date, the fucoidans are the most concerned by the scientific researchers owing to its pharmaceutical activities. Because not only the fucoidan contents in many algae are relatively high, but they have many pharmacological functions. It is most probably that they are exploited as the materials of new medicines. More delightfully, fucoidans have a number of interesting advantages. Firstly, they are water-soluble (as they belong to compounds of sulfate kind); secondly, fucoidans are easily absorbed by human body and they show no significant poisonous effect on human bodies. Presently Japanese researchers have separated 3 fucoidans with different molecular structures, i.e., G-, F-, and U-fucoidan. Results of animal experiments using the 3 fucoidans showed that they all have strong effects of facilitating the apoptosis of tumor cells (the effect of inhibiting the growth of tumors), equilibrating the immunity and promoting the regenesis of organism cells in the body, etc. It is hopeful that these 3 types of fucoidans can be exploited to be new clinic anti-tumor medicines.

Currently the studies on the weight reducing effects of fucoxanthin extract have got on primary advancement. However, the weight reducing effect is not yet ideal when it is used as the sole components and few studies has been carried out on the compositions of fucoxanthin extract.

SUMMARY OF THE INVENTION

To solve the shortcomings of the present techniques, the main object of this invention is to propose a composition.

On the one hand, this invention provides a kind of composition containing fucoxanthin extract, the said composition also contains tocotrienols and/or fucoidans.

In one preferable embodiment of this invention, the sources of the said fucoxanthin extract can be plants, microbes, or synthesized compounds. More preferably, the source of said fucoxanthin extract is plants, the said plants are algae. More preferably, said algae comprise one or more kinds of the following: kelp, gulfweed, bladder-wrack, *myosoton aquaticum, podocystis, chorda filum, undaria pinnatifida*, bull-kelp, carrageen, *sargassum kjellmanianum*, saltwort, *sargassum pallidum* and diatom.

In one preferable embodiment of this invention, the sources of the said tocotrienols can be plants, microbes, or synthesized compounds. More preferably, the source of said tocotrienols is plants. More preferably, said plant source is one or more kinds of the following: palm, rice and achiote. The tocotrienols can be one or more compounds selected from the following: α-Tocotrienol, β-Tocotrienol, γ-Tocotrienol or δ-Tocotrienol.

In one preferable embodiment of this invention, the source of said fucoidans is algae of the brown alga type, said algae of brown alga type comprises one or more types of the following: kelp, *undaria pinnatifida*, purple laver, saltwort, carrageen, *Gelidium amansii* and waterweed.

In one preferable embodiment of this invention, said composition also contains pharmaceutically acceptable adjuvants. Said adjuvants are selected from excipients, thickeners, dispersion media, coating materials, sweeteners, etc. Specifically, said adjuvants include but are not restricted within the following kinds of substances: diluting liquids, binders, lubricants, dispersants, colorants, expanders, flavoring materials, sweeteners and other composite materials normally used for specific therapy, such as buffering agents and adsorbents. The said adjuvants are added into the composition using the conventional techniques in this field. More preferably, said adjuvants are one or more substances selected from the following: denaturated starch, dextrin, median chain triglyceride oil, acacia gum, Tween 80, calcium phosphate.

In one preferable embodiment of this invention, the effective dose of fucoxanthin contained in said medicinal composition is between 0.1 mg-20 mg. More preferably, said dose of fucoxanthin is between 0.5 mg-15 mg. Most preferably, said dose of fucoxanthin is between 1 mg-10 mg.

In one preferable embodiment of this invention, the dose of tocotrienols contained in said composition is between 0.1 mg-50 mg. More preferably, said dose of tocotrienols is between 0.5 mg-40 mg. Most preferably, said dose of tocotrienols is between 1 mg-30 mg.

In one preferable embodiment of this invention, the content of fucoidan in said composition is between 0.1 mg-1000 mg. More preferably, said dose of fucoidan is between 1 mg-600 mg. More preferably, said dose of fucoidan is between 10 mg-500 mg.

In one preferable embodiment of this invention, the weight reducing composition proposed in this invention may be produced as preparations for intestinal therapy. Preferably, said preparations comprise hard- and soft capsules, tablets, medicinal granules, oral liquids and suspensions.

On the other hand, this invention proposes the application of said composition described in weight reducing, wherein the subjects of tests take said composite orally, said subjects are mammals.

In one preferable embodiment of this invention, said mammals are human.

In one preferable embodiment of this invention, said weight reducing effect is the decrease of the subjects' body weight.

In one preferable embodiment of this invention, said weight reducing effect is the decrease of the subjects' abdomen fat.

In one preferable embodiment of this invention, the daily dose of effective fucoxanthin ingredients the subjects take is between 0.1 mg-20 mg. More preferably, said daily dose of fucoxanthin is between 0.5 mg-15 mg. Most preferably, said daily dose of fucoxanthin is between 1 mg-10 mg.

In one preferable embodiment of this invention, the daily dose of tocotrienols the subjects take is between 0.1 mg-50 mg. More preferably, said daily dose of tocotrienols is between 0.5 mg-40 mg. Most preferably, said daily dose of tocotrienols is between 1 mg-30 mg.

In one preferable embodiment of this invention, the daily dose of fucoidan is between 0.1 mg-1000 mg. More preferably, said daily dose of fucoidan is between 1 mg-600 mg. Most preferably, said daily dose of fucoidan is between 10 mg-500 mg.

In one preferable embodiment of this invention, said daily dose is a single dose daily.

In one preferable embodiment of this invention, said daily dose is multiple doses daily.

The data from this invention showed that fucoxanthin has a certain weight reducing effect stronger than tocotrienols and fucoidan alone. When fucoxanthin and tocotrienols are applied in compositive manner, the two represent apparent synergistic effect. When fucoxanthin and fucoidan are applied in compositive manner, the two represent apparent synergistic effect, too. When three components of fucoxanthin, tocotrienols and fucoidan are applied in compositive manner, more significant synergistic effect is revealed and more effective weight loss can be achieved.

DETAILED DESCRIPTION OF THE INVENTION

Following are more detailed description, in combination with the experimental results, of the abovementioned and other technical characteristics and advantages of this invention.

Fucoxanthin is extracted from a group of following algae: kelp, gulfweed, bladder-wrack, *myosoton aquaticum, podocystis, chorda filum, undaria pinnatifida*, bull-kelp, carrageen, *sargassum kjellmanianum*, saltwort, *sargassum pallidum* and diatom. The pharmaceutically acceptable excipients include any solvent, dispersion medium, coating material, sweetener, etc. Said adjuvants specifically include but are not restricted within the following a group of substances: diluting liquids, adhesives, lubricants, dispersants, colorants, expanders, flavoring materials, sweeteners and other composite materials normally used for specific therapy, such as buffering agents and adsorbents. The said adjuvants are added into the composition using the conventional techniques in this field.

The composition stated in this invention can be prepared as any kind of common preparation, such as tablets, capsules, medicinal granules, oral liquids, suspensions and emulsion.

Preferably, it can be prepared as hard- and soft capsules, medicinal granules and oral liquids.

In this invention, appropriate ethanol water solution can be used to extract sea algae to obtain fucoxanthin extract, by adsorption of the fucoxanthins onto a separation medium, eluting with appropriate solvent, and subsequent concentration of the eluant, red fucoxanthin extract can be obtained. Specific preparation method can be referred to the Chinese Patent application No. CN200810226391.3 (A method for the purification of fucoxanthin).

After adding emulsifier, fucoxanthin thus obtained is emulsified uniformly, fucoidan and denaturated starch are subsequently added, stirred up, the mixture is spray dried. The spray dried powder is added with appropriate pharmaceutically accepted adjuvants, to prepare preparations for intestinal tract, including oral liquids, tablets, soft- and hard capsules and drop pills etc.

By mixing fucoxanthin and tocotrienols evenly, added with edible oil or median chain triglyceride oil, it is also possible to produce soft capsules, or the mixture can be emulsified into oil-in-water emulsion, and then added denaturated starch with stirred up, and subsequently spray dried. The spray dried powder is added with appropriate pharmaceutically accepted adjuvants to prepare preparations for intestinal tract, including oral liquids, tablets, soft- and hard capsules and drop pills etc.

The preparations may also be made by mixing fucoxanthin and tocotrienols evenly, the mixture is added with fucoidan and denaturated starch, stirred up, and subsequently spray dried. The spray dried powder is added with appropriate pharmaceutically accepted adjuvants to prepare preparations for intestinal tract, including oral liquids, tablets, soft- and hard capsules and drop pills etc.

The preparations may also be made by mixing Tween80 and PEG 400, stirred up thoroughly, the mixture is then added with vegetable oil or median chain triglyceride oil, and subsequently with fucoxanthin, tocotrienols, fucoidan and appropriate amount of thickener such as sodium carboxymethylcellulose, acacia gum and agar. The mixture is stirred up thoroughly and is then homogenized using a colloid mill or homogenizer. Subsequently, soft capsules can be produced by using glutin and glycerol as capsule shell material according to the manufacture method of soft capsules.

The preparations may also be made by dissolving fucoxanthin with organic solvents. The solution is added with an organic solution containing tocotrienols, subsequently fucoidan water solution and appropriate emulsifier, such as Tween or Span and denaturated starch water solution etc. The mixture is concentrated to a certain degree under reduced pressure and spray dried. The dried powder is added with silica and talcum powder, stirred up and milled thoroughly. This powder can be made into common preparations such as water-soluble beverages, medicinal granules and capsules according to the common procedures.

Following are further descriptions of this invention by examples. It should be understood that these examples are intended to exemplify the invention, not to restrict the protection range of this invention.

Example 1

Capsules prepared using ingredients including fucoxanthin extracts (see Table 1).

TABLE 1

Formulation of the Example 1

| Ingredients | content |
| --- | --- |
| fucoxanthin | 2 mg |
| fucoidan | 22 mg |
| tocotrienols | 2 mg |
| denaturated starch | 200 mg |

Example 2

Soft capsules prepared using ingredients including fucoxanthin extracts (see Table 2).

TABLE 2

Formulation of the Example 2

| Ingredients | content |
| --- | --- |
| fucoxanthin | 3.87 mg |
| fucoidan | 387 mg |
| tocotrienols | 58.06 mg |
| denaturated starch | 50 mg |
| *acacia* gum | 1 mg |

Example 3

Granules prepared using ingredients including fucoxanthin extracts (see Table 3).

TABLE 3

Formulation of the Example 3

| Ingredients | content |
| --- | --- |
| fucoxanthin | 2 mg |
| fucoidan | 1 g |
| tocotrienols | 5 mg |
| Tween 80 | 10 mg |
| Calcium phosphate | 2.5 mg |

Example 4

Test substances: Formulations are prepared according to the ratios shown in Table 4 Formulations for feeding animals: high-fat feed is composed of 80% basic feed, 10% lard and 10% yolk powder.

Grouping and treatment of the test animals: 80 grown-up male healthy SD clean grade rats (body weight 180-210 g) are adaptively fed with basic feed for a week, 10 are used as basic feed control, the rest are fed with high-fat feed. A month later, the group of rats fed with high-fat feed is randomly grouped into 7 groups according to their weights, 10 in each group: model control, fucoxanthin (A), tocotrienols(B), fucoidan (C), composition A+B+C, composition A+B and composition A+C. The group of basic feed keeps on feeding with basic feed, the rest groups are fed with high-fat feeds. The groups of basic feed and model control are intragastrically administrated with distilled water, the rest groups are intragastrically administrated with tested medicines, all administrated for 30 d. The groups of animals are raised in different cages in rooms with the temperature conditioned at $(22\pm2)$ ° C. and under natural illumination. The rats take food and water freely. Each week, their body weights are measured and the amounts of food they take are observed and recorded. They are weighted after feeding for 30 d.

Statistical analysis: the variance from the data collected in this experiment is analyzed with SAS package, Dunnett's t test is used to compare statistically the results from different groups, the results of P<0.05 is decided as statistically significant.

The results: According to the experimental results, the food-intake of the groups of rats did not change with the time they were administrated with medicines, thus no statistical significance is detected and this is no longer depicted later on. From Table 5 it can be seen that when the experiment finished, the difference in weights of the animals in model control was statistically significant (P<0.05), this means that the modeling of rat obesity promotion model was successful.

At the same time, weights of rats in A+B+C, A+B, A+C groups decreased further and differed from the model control (P<0.05, P<0.01), this means that the composition containing fucoxanthin (A) had weight reducing effect on obese rats, and the weight reducing effects of composition A+B+C, A+B, A+C were more significant than fucoxanthin (A) alone (P<0.01).

TABLE 4

Formulation of the Example 4

| Group | Oral dose by each rat |
|---|---|
| A(fucoxanthin) | 36.25 μg |
| B(tocotrienols) | 36.25 μg |
| C(fucoidan) | 0.4 mg |
| A + B + C | A: 36.25 μg; B: 36.25 μg; C: 0.4 mg |
| A + B | A: 36.25 μg; B: 36.25 μg; |
| A + C | A: 36.25 μg; C: 0.4 mg |

TABLE 5 the effect of different groups of medicine administration in Example 4 on the body weight of model rats with alimentary obesity. ($\bar{x} \pm s$) g

| Group | Body weight (g) (before experiment) | Body weight (g) (after experiment) | Weight increased(g) |
|---|---|---|---|
| Control with basic feed | 438.21 ± 21.20 | 469.43 ± 32.78 | 31.22 ± 19.87 |
| Model control | 485.98 ± 20.45* | 547.28 ± 35.52* | 61.30 ± 21.22* |
| C | 486.69 ± 21.12 | 546.59 ± 18.64 | 59.90 ± 18.11 |
| B | 486.13 ± 20.98 | 545.02 ± 21.10 | 58.89 ± 20.25 |
| A | 486.50 ± 22.10 | 530.18 ± 20.32Δ | 43.68 ± 19.13Δ |
| A + C | 485.96 ± 20.11 | 516.08 ± 20.13ΔΔ | 30.12 ± 18.22ΔΔ |
| A + B | 485.99 ± 20.44 | 515.49 ± 39.21ΔΔ | 29.50 ± 18.21ΔΔ |
| A + B + C | 485.55 ± 21.10 | 511.10 ± 21.00ΔΔ | 25.55 ± 21.52ΔΔ |

(*P<0.05 in comparison with the control group with basic feed group; ΔP<0.05, ΔΔP<0.01 in comparison with the model control group)

Example 5

The procedure was the same as in Example 4. The formulation is shown in Table 6. After feeding for 30 d and weighing, executing all the rats, the abdomen fat was peeled off and weighed accurately. Statistical analysis was carried out as in Example 4

The results: From Table 7 it can be seen that body weights, weights of abdomen fat as well as the ratios of abdomen fat weight/body weight of the animals in model control groups were statistically significant (P<0.05) in comparison with the group fed with basic feed, this means that the modeling of rat obesity promotion model was successful.

In the meantime, body weights, weights of abdomen fat as well as the ratios of abdomen fat weight/body weight of rats in A+B+C, A+B, A+C and A groups decreased further (P<0.05) and differed from the model control, this means that the composition containing fucoxanthin (A) had weight reducing effect on obese rats, and the weight reducing effects of composition A+B+C, A+C, A+B were more significant than fucoxanthin (A) alone.

TABLE 6 the formulation of the Example 5

| Component | Oral dose by the Rats |
|---|---|
| A (fucoxanthin) | 9.06 μg |
| B (tocotrienols) | 36.25 μg |
| C (fucoidan) | 18.12 mg |
| A + B + C | A: 9.06 μg; B: 36.25 μg; C: 18.12 mg |
| A + C | A: 9.06 μg; C: 18.12 mg |
| A + B | A: 36.25 μg; B: 36.25 μg; |

TABLE 7 the effect of different groups of medicine administration in Example 5 on the abdomen fat in model rats with alimentary obesity ($\bar{x} \pm s$) g

| Group | Body weight (g) (after experiment) | Abdomen fat (g) | Weight of abdomen fat/body weight |
|---|---|---|---|
| Control with basic feed | 469.43 ± 32.78 | 8.98 ± 2.04 | 1.92 ± 0.11 |
| Model control | 547.28 ± 35.52 | 13.29 ± 1.23* | 2.43 ± 0.22* |
| C | 546.59 ± 18.64 | 12.99 ± 1.23 | 2.38 ± 0.13 |
| B | 545.02 ± 21.10 | 12.87 ± 2.11 | 2.36 ± 0.16 |
| A | 530.18 ± 20.32 | 9.58 ± 1.99Δ | 1.81 ± 0.13Δ |
| A + C | 516.08 ± 20.13 | 9.19 ± 1.97ΔΔ | 1.78 ± 0.12ΔΔ |
| A + B | 515.49 ± 39.21 | 9.01 ± 2.01ΔΔ | 1.75 ± 0.11ΔΔ |
| A + B + C | 511.1 ± 21.00 | 8.44 ± 1.98ΔΔ | 1.65 ± 0.14ΔΔ |

(*P<0.05, in comparison with the control group with basic feed group; ΔP<0.05, ΔΔP<0.01 in comparison with the model control group)

Example 6

The procedure was the same as in Example 4. The formulation is shown in Table 8. After feeding for 30 days and weighing, executing all the rats, the fat pads around the testicles were peeled off and weighed accurately. Statistical analysis was carried out as in Example 4.

The results: From Table 9 it can be seen that body weights, the ratios of fat pad weights around testicles/body weight of the animals in model control groups were statistically significant (P<0.05) in comparison with the group fed with basic feed, this means that the modeling of rat obesity promotion model was successful.

At the same time, body weights, the fat pad weights around the testicles as well as the ratio of fat pad weight around the testicles/body weight of rats in A+B+C, A+B, A+C and A groups decreased (P<0.05) and differed from the model control, this means that the composition containing fucoxanthin (A) had weight reducing effect on obese rats, and the weight reducing effects of the composition were more significant than fucoxanthin (A) alone.

TABLE 8

Formulation of the Example 6

| Component | Oral dose by the rats |
|---|---|
| A (fucoxanthin) | 362.5 μg |
| B (tocotrienols) | 18.12 μg |
| C (fucoidan) | 9.06 mg |
| A + B + C | A: 362.5 μg; B: 18.12 μg; C: 9.06 mg |
| A + C | A: 362.5 μg; C: 9.06 mg |
| A + B | A: 362.5 μg; B: 18.12 μg |

TABLE 9

The effect of different groups of medicine administration in Example 6 on the fat around the testicles in model rats with alimentary obesity ($\bar{x} \pm s$) g

| Group | Body weight (g) (after experiments) | Fat pad weight around the testicles (g) | Fat pad weight around the testicles/body weight |
|---|---|---|---|
| Control with basic feed | 469.43 ± 32.78 | 6.44 ± 0.88 | 1.37 ± 0.15 |
| Model control | 547.28 ± 35.52* | 9.21 ± 0.51* | 1.68 ± 0.14* |
| C | 546.59 ± 18.64 | 9.11 ± 0.48 | 1.67 ± 0.13 |
| B | 545.02 ± 21.10 | 9.10 ± 0.79 | 1.67 ± 0.10 |
| A | 530.18 ± 20.32 | 7.32 ± 0.83Δ | 1.38 ± 0.11Δ |
| A + C | 516.08 ± 20.13 | 6.71 ± 0.72ΔΔ | 1.30 ± 0.11ΔΔ |
| A + B | 515.49 ± 39.21 | 6.44 ± 0.85ΔΔ | 1.25 ± 0.12ΔΔ |
| A + B + C | 511.1 ± 21.00 | 6.23 ± 0.73ΔΔ | 1.22 ± 0.13ΔΔ |

(*$P < 0.05$, in comparison with the group fed with basic feed group; Δ$P < 0.05$, ΔΔ$P < 0.01$ in comparison with model control group)

Example 7

The procedure was the same as in Example 4. The formulation is shown in Table 10. After feeding for 30 d and weighing, executing all the rats, the fat pads around the kidneys were taken out and weighed accurately. Statistical analysis was carried out as in Example 4.

The results: From Table 11 it can be seen that body weights, the fat pad weights around the kidneys as well as the ratios of fat pad weights around the kidneys/body weight of the animals in model control groups were statistically significant ($P<0.05$) in comparison with the group fed with basic feed, this means that the modeling of rat obesity promotion model was successful.

At the same time, body weights, the fat pad weights around the kidneys as well as the ratio of fat pad weight around the kidneys/body weight of rats in A+B+C, A+C, A+B and A groups decreased ($P<0.05$) and differed from the model control, this means that the composition containing fucoxanthin (A) had weight reducing effect on obese rats, and the weight reducing effects of the composition were more significant than fucoxanthin (A) alone.

TABLE 10

Formulation of the Example 7

| Component | Oral dose by the rats |
|---|---|
| A (fucoxanthin) | 181.23 μg |
| B (tocotrienols) | 398.7 μg |
| C (fucoidan) | 1.81 mg |
| A + B + C | A: 181.23 μg; B: 398.7 μg; C: 1.81 mg |
| A + B | A: 181.23 μg; B: 398.7 μg |
| A + C | A: 181.23 μg; C: 1.81 mg |

TABLE 11

Effect of different groups of medicine administration in Example 7 on the fat around the kidneys in model rats with alimentary obesity ($\bar{x} \pm s$) g

| Group | Body weight (g) (after experiments) | Total weight of fat pads around the kidneys (g) | Total weight of fat pads around the kidneys/body weight |
|---|---|---|---|
| Control with basic feed | 469.43 ± 32.78 | 5.57 ± 0.46 | 1.19 ± 0.12 |
| Model control | 547.28 ± 35.52* | 9.97 ± 0.65* | 1.82 ± 0.13* |
| C | 546.59 ± 18.64 | 9.29 ± 0.61 | 1.70 ± 0.13 |
| B | 545.02 ± 21.10 | 9.18 ± 0.60 | 1.68 ± 0.11 |
| A | 530.18 ± 20.32 | 7.42 ± 0.60Δ | 1.42 ± 0.12Δ |
| A + C | 516.08 ± 20.13 | 6.86 ± 0.50ΔΔ | 1.33 ± 0.11ΔΔ |
| A + B | 515.49 ± 39.21 | 6.70 ± 0.62ΔΔ | 1.30 ± 0.12ΔΔ |
| A + B + C | 511.1 ± 21.00 | 6.13 ± 0.58ΔΔ | 1.20 ± 0.14ΔΔ |

(*$P < 0.05$, in comparison with the control group with basic feed; Δ $P < 0.05$, ΔΔ $P < 0.01$ in comparison with the model control)

Example 8

Clinic Intake Trial Experiment

To examine the weight reducing effect of fucoxanthin composition by means of random control method, 20 eligible test subjects of the age of 20 to 50 were divided into 5 groups, A+B+C, A+C, A+B, A, B+C, with random figure table method. The number of the subjects in each group was n=4. The daily doses of the medicines taken by the subjects were according to Table 12. Apart from being administrated with each of the different tested medicines at the breakfast time according to the set way of taking the medicine, other normal life style and dietetic habit of the subjects were not changed. No low-calorie food recipe was required, no restriction to the food and drink was executed and no extra physical training was carried out. To examining the effect of sampling of the medicine, the subjects were respectively examined before sampling of the medicine and 1 month, 2 and 3 months after the sampling. That is, the bodyweight, waist- and hiplines, blood sugar and blood fat were measured, abdomen CT scanning was carried out and so on. The subjects were periodically followed-up to find out the experiences and to supervise and guarantee compliance of the customers in taking the medicine. For the test, those suffered from serious metabolic diseases that need medicinal control and those taken other weight reducing products had been excluded.

Abdomen fat areas were measured with CT
Instrument: CT Model Pronto; Hitachi, Japan.
120 kV, 175 mA
Layer thickness of the scanning: 10 mm
Scanning in the umbilical cross-section
Attenuation of the adipose tissue: −250~−50 HU (CT Unit)
Calculation of the fat areas: total abdomen fat, visceral- and subcutaneous fat (mm$^2$)

Using CT Scanning, total fat—as well as visceral fat areas were marked out across the umbilical cross-section, the areas were measured respectively, the area of subcutaneous fat was obtained as the difference of both areas.

The changes of body weights, abdomen total fat areas, visceral fat areas as well as subcutaneous fat areas of the test subjects before and after clinic experiments are shown in Tables 13 and 14.

The results of CT scanning showed that body weights, weights of total abdomen fat, the weights of visceral- and subcutaneous fat of rats fed with the composition containing fucoxanthin all decreased. The effect reduced body weight by the composition of fucoxanthin is correlated with the decrease of abdomen fat. The effects of A+B+C, A+C, A+B, and A groups are more significant than B+C group (P<0.05) and the weight reducing effects of compositions were more significant than fucoxanthin (A) alone. The indices of weight reducing effect of the A+B+C group is significantly superior to other groups, followed by the A+B group and followed by the A+C group.

Other Examinations

No abnormity has been found in blood routine examination, urine routine examination, liver function, blood pressure, heart rate and blood sugar.

In the follow-up questionnaires, some questions were set up to find out the experiences as well as compliance of the customers in taking the medicine. The results of the questionnaire are as follows:

No phenomena of restraining of appetite, nausea, vomiting, discomfort of stomach and intestines happened in the digestive systems of the customers.

No phenomena of thirst, polyuria and frequent urination happened.

No phenomena of dysphoria, insomnia and night sweat happened in the psychosis.

No phenomena of rise of blood pressure and heart rate or heart-throb and dizziness happened.

Unlike traditional weight reducing products of the appetite restraining type functioning by means of the control of fat intake, the weight reducing effect of fucoxanthin composition is based on the fat metabolism and is not related to appetite, therefore, theoretically, unlike other weight reducing products that will cause the resumption of the appetite, and hence the body weight rebound after giving up taking the medicine, fucoxanthin compositions will exert continuous weight reducing effect and they can eliminate various unfavorable side effects. When the fucoxanthin compositions are stopped administering for a month, the body weight of subjects does not rebound and therefore it is unnecessary to change the life style, to resort to be on diet or clapped-out physical exercise. The medicines can be taken by way of single doses as well as multiple doses, this makes fucoxanthin preparations more convenient. Therefore, the composition composed of fucoxanthin and fucoidan, of fucoxanthin and tocotrienol, and of fucoxanthin, fucoidan and tocotrienol are types of safe, effective and convenient ideal weight reducing product. Fucoxanthin compositions have more significant weight reducing effect than fucoxanthin alone. It can be taken reassuringly by those populations taking health-care, reducing weight and taking other medicines in same time and the weight reducing effect is trustworthy. These weight reducing compositions can also be applied as food additives, foodstuffs, health products, and medicines.

TABLE 12

| | Oral doses |
|---|---|
| Clinic groups | daily dose |
| A | 2 mg |
| A + B + C | A: 2 mg; B: 2 mg; C: 22 mg |
| A + B | A: 2 mg; B: 2 mg; |
| A + C | A: 2 mg; C: 22 mg |
| B + C | B: 2 mg; C: 22 mg |

A: fucoxanthin;
B: tocotrienols;
C: fucoidan

TABLE 13

Changes of body weights as well as total abdomen fat area of the test subjects.

| | Body weight ($\bar{x} \pm s$) Kg | | | Total abdomen fat area ($\bar{x} \pm s$) mm$^2$ | | |
|---|---|---|---|---|---|---|
| Groups n = 4 | Before clinic experiment | After clinic experiment | Change | Before clinic experiment | After clinic experiment | decrease |
| B + C | 70.4 ± 0.10 | 70.54 ± 0.14 | increase by 0.21% | 36780 ± 1706 | 36725 + 1389 | 0.15% |
| A | 68.4 ± 0.13 | 67.37 ± 0.11 | decrease by 1.5% | 36555 ± 1645 | 34479 ± 1475 | 5.68% |
| A + C | 69.3 ± 0.14 | 69.3 + 0.13 | decrease by 2.5% | 36666 ± 1558 | 32816 ± 1345 | 10.50% |
| A + B | 70.4 ± 0.11 | 68.29 ± 0.14 | decrease by 3.0% | 36700 ± 1424 | 32535 ± 1169 | 11.35% |
| A + B + C | 71.5 ± 0.12 | 67.93 ± 0.10 | decrease by 5% | 37000 ± 1315 | 29999 ± 1268 | 18.92% |

TABLE 14

Changes of the area of visceral- and subcutaneous fat of the experimental subjects

| | The area of visceral fat ($\bar{x} \pm s$) mm$^2$ | | | The area of subcutaneous fat ($\bar{x} \pm s$) mm$^2$ | | |
|---|---|---|---|---|---|---|
| Groups n = 4 | Before clinic experiment | After clinic experiment | Decrease (%) | Before clinic experiment | After clinic experiment | Decrease (%) |
| B + C | 17493 ± 1454 | 17477 ± 1545 | 0.09% | 15488 ± 1058 | 15469 ± 1157 | 0.12% |
| A | 17380 ± 1185 | 16650 ± 1484* | 4.20% | 15514 ± 1192 | 14568 ± 1225* | 6.10% |
| A + C | 17400 ± 1087 | 16158 ± 1327* | 7.14% | 15498 ± 1386 | 14026 ± 1532* | 9.50% |
| A + B | 17484 ± 1378 | 15986 ± 1164* | 8.57% | 15480 ± 1454 | 13932 ± 1345* | 10.00% |
| A + B + C | 17500 ± 1554 | 14999 ± 1289* | 14.29% | 15500 ± 1512 | 12916 ± 1487* | 16.67% |

(*P < 0.05 in comparison with B + C)

The above are preferable examples of this invention, which are intended to exemplify the invention, not to restrict the protection range of this invention. Within the spirit and scope limited by the claims of the present invention, the person skilled in the art can make lots of change, modification, which should be fallen within the protection scope of the invention.

The invention claimed is:

1. A method of reducing a weight of a subject, the method comprising administering to the subject in need thereof an effective amount of a composition comprised of fucoxanthin extract, tocotrienol, and fucoidan, wherein the subject is a mammal.

2. The method of claim 1, wherein the mammal is a human.

3. The method of claim 2, wherein the weight is a body weight of the subject.

4. The method of claim 1, wherein the weight is an abdomen fat weight of the subject.

5. The method of claim 1, wherein a daily dose of fucoxanthin taken by the subject is between 0.1 mg-20 mg.

6. The method of claim 5, wherein said daily dose is a single dose daily.

7. The method of claim 5, wherein said daily dose is multiple doses daily.

8. The method of claim 1, wherein a daily dose of the tocotrienol taken by the subject is between 0.1 mg-50 mg.

9. The method of each of claim 8, wherein said daily dose is a single dose daily.

10. The method of each of claim 8, wherein said daily dose is multiple doses daily.

11. The method of claim 1, wherein a daily dose of the fucoidan taken by the subject is between 0.1 mg-1000 mg.

12. The method of each of claim 11, wherein said daily dose is a single dose daily.

13. The method of each of claim 11, wherein said daily dose is multiple doses daily.

14. The method of claim 1, wherein a source of the fucoxanthin extract is selected from the group consisting of a plant, a microbe, a synthesized compound, and a combination thereof.

15. The method of claim 14, wherein the source of the fucoxanthin extract is sea algae selected from the group consisting of kelp, gulfweed, bladder-wrack, myosoton *aquaticum*, podocystis, *chorda filum, undaria pinnatifida*, bull-kelp, carrageen, *sargassum kjellmanianum*, saltwort, *sargassum pallidum*, diatom, and a combination thereof.

16. The method of claim 1, wherein the tocotrienol is selected from the group consisting of α-tocotrienol, β-tocotrienol, γ-tocotrienol, δ-tocotrienol, and a combination thereof.

17. The method of claim 1, wherein a source of the fucoidan is sea algae of brown alga type.

18. The method of claim 1, wherein the composition further comprises a pharmaceutically acceptable adjuvant.

19. The method of claim 1, wherein the composition is a preparation for intestinal tract.

20. The method of claim 19, wherein said preparation comprises a hard-capsule, a soft capsule, a tablet, a medicinal granule, an oral liquid, a suspension, or an emulsion.

* * * * *